US006685772B2

(12) United States Patent
Goddard, III et al.

(10) Patent No.: US 6,685,772 B2
(45) Date of Patent: Feb. 3, 2004

(54) DE NOVO PROCESSING OF ELECTRONIC MATERIALS

(75) Inventors: William A. Goddard, III, Pasadena, CA (US); Gyeong S. Hwang, Austin, TX (US)

(73) Assignee: California Institute of Technology, Pasadena, CA (US)

( * ) Notice: Subject to any disclaimer, the term of this patent is extended or adjusted under 35 U.S.C. 154(b) by 67 days.

(21) Appl. No.: 10/113,919

(22) Filed: Mar. 28, 2002

(65) Prior Publication Data

US 2002/0188373 A1 Dec. 12, 2002

Related U.S. Application Data

(60) Provisional application No. 60/280,140, filed on Mar. 29, 2001, and provisional application No. 60/279,628, filed on Mar. 28, 2001.

(51) Int. Cl.[7] .................................................. C30B 1/10
(52) U.S. Cl. ..................... 117/3; 117/4; 117/19; 117/55; 117/85; 117/86; 438/4
(58) Field of Search ........................... 117/3, 4, 19, 85, 117/86, 55; 438/4

(56) References Cited

U.S. PATENT DOCUMENTS

| 4,053,924 | A | * | 10/1977 | Roman et al. ............... 257/655 |
| 4,400,221 | A | * | 8/1983 | Rahilly ........................ 438/74 |
| 4,801,557 | A | * | 1/1989 | Wessels et al. ............... 117/91 |
| 5,709,745 | A | * | 1/1998 | Larkin et al. ................. 117/96 |
| 5,862,057 | A | * | 1/1999 | Xia et al. ..................... 716/21 |

OTHER PUBLICATIONS

Semiconductors and Semimetals, Willardson Academic Press 1984 vol 20 chapter 4.*

* cited by examiner

*Primary Examiner*—Robert Kunemund
(74) *Attorney, Agent, or Firm*—Fish & Richardson P.C.

(57) ABSTRACT

Computer programs and computer-implemented methods for predicting from first principles the behavior of dopants and defects in the processing of electronic materials. The distribution of dopant and defect components in a substrate lattice is predicted based on external conditions and fundamental data for a set of microscopic processes that can occur during material processing operations. The concentration behavior of one or more fast components is calculated in two stages, by solving a first relationship for a time period before the fast component reaches a pseudo steady state at which the concentration of the fast component is determined by concentrations of one or more second components, and by solving a second relationship for a time period after the first component reaches the pseudo steady state. Application of these methods to modeling ultrashallow junction processing is also described.

30 Claims, 8 Drawing Sheets

DE NOVO PROCESSING OF ELECTRONIC MATERIALS

CROSS-REFERENCE TO RELATED APPLICATIONS

This application claims the benefit of Provisional Application Nos. 60/279,628, filed on Mar. 28, 2001, and 60/280,140, filed on Mar. 29, 2001, both of which are incorporated by reference herein.

BACKGROUND

The invention relates to semiconductor processing and the prediction of structures and properties resulting from processes used in the preparation and modification of semiconductor materials.

In order to maximize the performance and value of electronic devices including memories, central processor units (CPUs), transmitters and detectors of electromagnetic and sonic radiation, and other components of electronic computers, it is important to reduce the size, noise, and reproducibility while increasing the speed of the devices. This requires growing complex heterostructures in which various dopants are introduced into precise locations and processed to obtain desired distributions, electrical activity, and other properties useful in devices. To optimize the performance of these devices, it is necessary to model and simulate the electrical and mechanical properties resulting from various distributions and clustering of the dopants, oxidation products, and impurities. With previous technologies, modeling and simulation techniques have generally treated the materials as a macroscopic continuum, with continuous variations in concentrations of dopants and, and have used finite element analysis to describe the diffusion and operation of the devices.

In future generations of devices, the size of device elements (for example the gate of a field effect transistor (FET)) will be in the range of less than 100 nm, where it will be important to consider the atomistic characteristics of the materials, rather than just their macroscopic continuum properties. For example, to make a p-type silicon FET with gates less than 100 nm, it is useful to carry out ultrashallow ion implantation deposition of boron, using low energies (e.g., ~1 keV) that limit the boron to a region within a short distance (e.g., 20 nm) of the surface. To obtain optimal activity, it is useful to deposit sufficiently high boron surface concentrations (e.g., $5 \times 10^{20}$) near the surface to obtain sufficient activity of dopants for optimum performance. However, it is found that such conditions may lead to a clustering of the dopants and of other defects (vacancies and interstitials) and to long-range diffusion tails that degrade the performance, whereas it is desired to maintain the boron near the surface while unclustered in a substitutional site that maximizes performance. In addition it can happen that too much of the boron near the surface may diffuse to the interface, resulting in a kink or non-optimum distribution in the boron distribution. Also, much of the boron may not have the proper electrical activity (as a low energy acceptor level) due to clustering or association with a non-optimum site. These examples consider boron because there are serious problems today involving such systems; however, similar problem can occur for other dopants.

In order to develop the highest performance devices, it is important to accurately predict such properties as the distribution of the dopants and defects (e.g., vacancies, interstitials) as a function of depositing conditions and subsequent heat treatments (e.g. annealing), oxidation, exposure to other impurities or dopants, changes in external conditions (pressure, stress, voltage, magnetic fields, electromagnetic radiation, ultrasonic radiation, etc.). In addition, it is important to predict the electrical activity and other device properties resulting from the deposition and processing of such systems. Also, it is important to predict the critical voltages and fields for electrical or mechanical breakdown of such systems. In addition, it is important to predict the effects of aging (repeated cycling of voltages, stresses, temperature, and exposure to radiation, oxygen, water, and other molecules).

SUMMARY

The invention provides a prescription for a strategy and provides the associated computational techniques for predicting from first principles the structures and properties of electronic materials as a function of processing and operating conditions. These techniques can include quantum mechanics, development of force fields (FF) from the quantum mechanics (QM) or experiment, molecular dynamics (MD) using such FF or using QM, continuum mechanics based on parameters extracted from the molecular dynamics (MD) and elsewhere, and, preferably, combinations of two or more of these. Quantum mechanics (QM) calculations can be used to predict the electronic states and structures of the materials likely to be constructed for various processing conditions of interest. This includes various dopants (e.g., B or P), impurities (e.g. H and O) and defects (e.g. vacancies and interstitials) that might result from the synthesis and processing of the materials. The QM and can provide information on the rates of diffusion of the various impurities and defects and of formation of clusters and other structures. Using molecular dynamics techniques, fundamental rate parameter data from such quantum mechanics calculations or other sources can be used to estimate rates of processes such as diffusion, association and dissociation for collective systems (which can include, e.g., microscopic, mesoscale and macroscopic systems) that contain distributions of several or many kinds of defects and/or impurities. Finally, using continuum mechanics this data, and the fundamental data (e.g., from quantum mechanical and MD calculations), can be used to predict the distributions of dopant and defect structures and clusters as a function of external conditions.

In general, in one aspect, the invention provides methods and apparatus, including computer program apparatus, implementing techniques for predicting the behavior of dopant and defect components in a substrate lattice formed from a substrate material. The techniques include obtaining fundamental data for a set of microscopic processes that can occur during one or more material processing operations, and predicting a distribution of dopant and defect components in the substrate lattice based on the fundamental data and a set of external conditions. The fundamental data includes data representing the kinetics of processes in the set of microscopic processes and the energetics and structure of possible states in the material processing operations. The distribution of each first component is predicted by calculating the concentration of the first component for a time period before the first component reaches a pseudo steady state by solving a first relationship and calculating the concentration of the first component for a time period after the first component reaches the pseudo steady state by solving a second relationship based on one or more second components. The pseudo steady state is a state in which the concentration of the fast component is determined by concentrations of the second components.

Particular implementations can include one or more of the following features. The first components can include fast components having a high diffusivity or a high dissociation rate. The second components can include slow components having a low diffusivity or a low dissociation rate. For each of the first components, the first relationship can be solved with a time step determined based on the diffusivity and the dissociation rate of the corresponding first component. The first relationship can be an equation:

$$\frac{\partial C_k}{\partial t} = \nabla(D_k \nabla C_k) + K_{R,ij}C_iC_j + K_{D,m}C_m - K_{R,kl}C_kC_l - K_{D,k}C_k$$

where $D_k$ and $C_k$ are the mobility and the concentration of a component k, respectively. In this equation, the first term in the right-hand side represents diffusion of the component k; the second and third terms represents generation of the component k by i+j clustering (i+j→k) and m dissolution (m→k+l), respectively; and the fourth and fifth terms represent destruction of the component k by (k+l→m) and (k→i+j), respectively. The clustering and dissolution coefficients are given by $$K_{R,ij} = 4\pi R_p(D_i + D_j)$$

$$K_{D,k} = (n_H/4)K_{R,ij}\exp(-E_{b,k}/k_BT)$$

where $R_p$ is the capture radius, $n_H$ is the concentration of lattice sites in the substrate lattice, $E_b$ is the dissociation energy of k into i and j, $k_B$ is the Boltzmann constant, and T is the substrate temperature of the substrate lattice. The second relationship can be given by equation:

$$\nabla(D_k \nabla C_k) + K_{R,ij}C_iC_j + K_{D,m}C_m - K_{R,kl}C_kC_l - K_{D,k}C_k = 0$$

The techniques can also include calculating reaction information based on the fundamental data. The reaction information can identify major components and reactions from a set of possible components, and major reaction pathways for the processes of the set of microscopic processes. The distribution of dopant and defect components in the substrate lattice can then be predicted based on the fundamental data, the external conditions and the reaction information.

The microscopic processes can include, for example, diffusion, clustering and dissociation of dopant and/or defect components in the substrate lattice. The fundamental data can include, for example, data representing the dissolution rate of defect components, the mobility of mobile species and the binding energy of clusters. The set of external conditions can include initial concentrations for each dopant and defect component, and an initial temperature. The material processing operations can include, for example, heat treatments, oxidation, exposure to impurities, or changes in pressure, stress, voltage, magnetic fields, electromagnetic radiation or ultrasonic radiation.

The fundamental data can be calculated in a quantum mechanics calculation. The reaction information can be calculated in a kinetic Monte Carlo simulation. Predicting the distribution of dopant and defect components in the substrate lattice can include predicting a plurality of distributions of dopant and defect components in the substrate lattice for each of a plurality of different sets of external conditions. The techniques can also include selecting a desired distribution from the predicted distributions, and controlling a manufacturing process based on the set of external conditions corresponding to the selected distribution. The material processing operations can define a procedure for boron doping of silicon substrates, and the set of microscopic processes include the formation, diffusion and dissolution of substitutional boron-interstitial boron pairs in a silicon substrate lattice.

In preferred implementations, the invention thus provides techniques for predicting the structures and properties, such as distribution and clustering of dopants and impurities, that result from implantation, annealing, and other processes for preparing and modifying materials, and for predicting the electrical activity of the system as a function of processing conditions, manufacturing, aging, and application of external fields and conditions. These techniques can be implemented to realize one or more of the following advantages. Accurate prediction of such properties as the distribution of the dopants and defects, electrical activity, critical voltages and fields for electrical or mechanical breakdown, and the effects of aging, and modeling and simulating the structures and properties of devices as a function processing and operating conditions, can make possible the design of improved composition and processing conditions to develop improved properties, reliability and aging, while minimizing cost and failure. Using these techniques to monitor one or more device characteristics during production and compare the monitored characteristics to predicted optima can make possible the incorporation of increased automation into control systems for operating the processes. Prediction of performance as a function of aging and operating conditions can make it possible to develop improved fault tolerant systems.

The details of one or more embodiments of the invention are set forth in the accompanying drawings and the description below. Other features, objects, and advantages of the invention will be apparent from the description and drawings, and from the claims.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
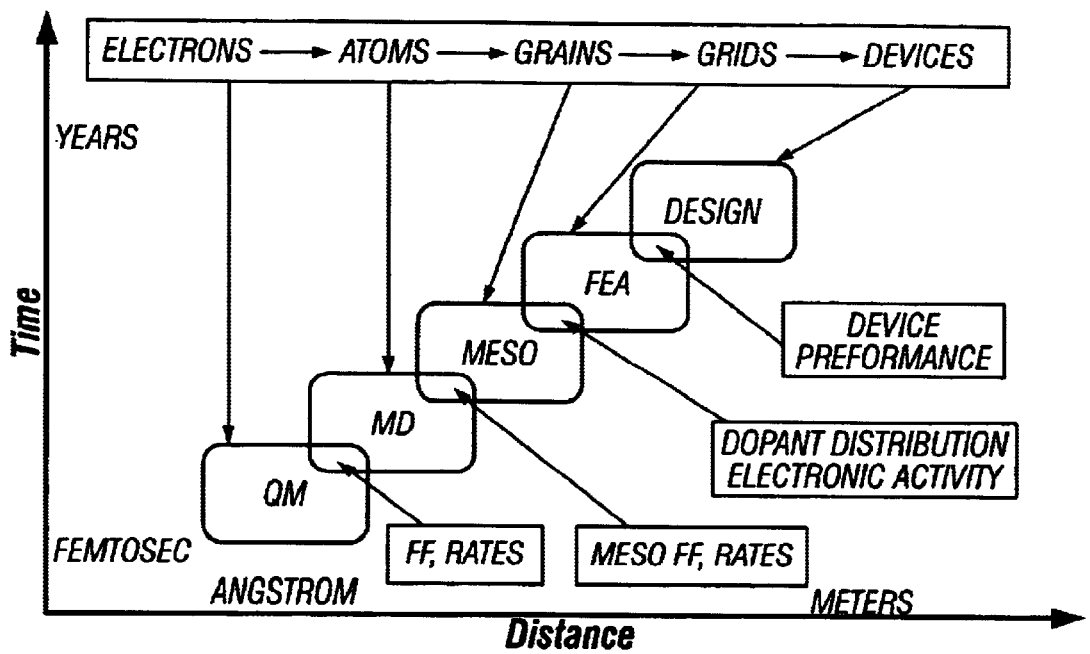
FIG. 1 illustrates a general approach to the de novo processing of electronic materials (DeN-PEM) according to the invention.

FIG. 1 illustrates a general approach to the de novo processing of electronic materials (DeN-PEM). Quantum mechanics calculations are used to predict from first principles the electronic states and structures of the materials likely to be constructed for various processing conditions of interest.

Figure 2:
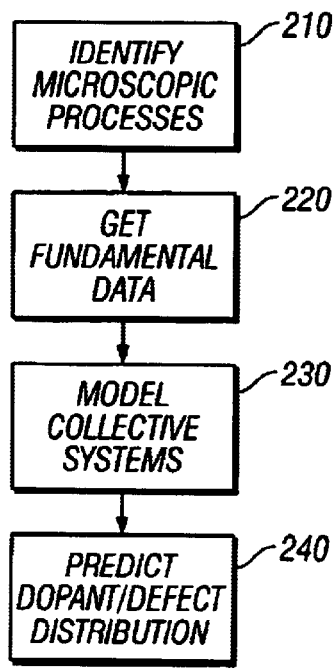
FIG. 2 is a flow diagram illustrating a general multiscale method of modeling electronic device processing according to the invention.
Figure 3:
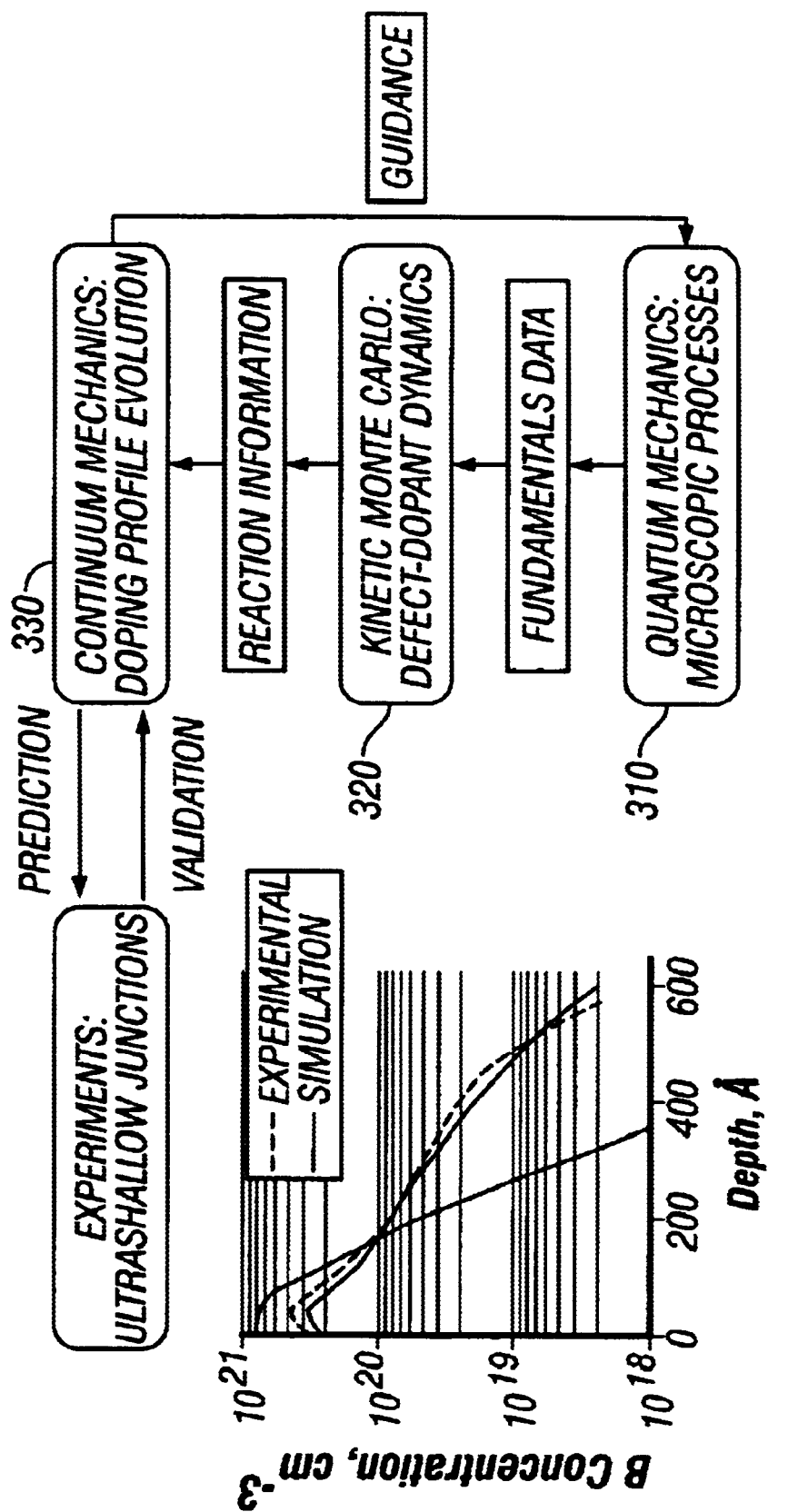
FIG. 3. illustrates the application of a multiscale modeling method to ultrashallow junction processing.

A multiscale method 200 of modeling electronic device processing is illustrated in FIG. 2. In a first step, one or more microscopic processes that may occur during a processing operation or operations are identified (step 210). Processing operations can include any conventional techniques used in the processing of electronic materials, such as the implantation of boron into a silicon lattice. The microscopic processes can include any processes that do or might occur during the operation(s), including the association of dopants, substrate atoms, and/or impurities to form clusters or complexes, the diffusion of such complexes and dopant components, the dissociation of complexes, and the like. Next, fundamental data are obtained for the microscopic processes of interest (step 220). Quantum mechanics (QM) calculations can be used in this step to predict the energetics and structures for the various states, the barriers for the various processes in which atoms and defects move from site to site, and the other data required to predict the rates of various processes such as diffusion, association and dissociation. This can be done by calculating the relative energy of the various stable structures and the activation energies and entropies for the various dynamic and kinetic processes that connect the various sites. For example, the activation entropy can be obtained from vibrational densities of states for bound and transition states. In addition, the QM calculation of band states and electrical activity can provide parameters relevant for predicting the electronic properties (e.g., conductivity, Hall effect, magneto-resistance, thermoelectric power) for various collections of substitutional, interstitial, and clusters of dopants and defects, and impurities. Quantum mechanics calculations can be performed, for example, using density functional theory as implemented in the known CPMD V3.3 package (J. Hutter, A. Alavi, T. Deutch, M. Bernasconi, S. Goedecker, D. Marx, M. Tuckerman, and M. Parrinello, MPI fuer Festkoerperforschung and IBM Zurich Research Laboratory 1995–1999) or other known techniques (e.g. programs such as Castep and DMOL3 as distributed by Accelrys Inc (San Diego) and Jaguar as distributed by Schrodinger Inc, Portland Oreg.). Specification of starting parameters for the calculations will depend on the system(s) to be modeled. In some cases it can be generated by starting with a known crystal structure and using statistical techniques (e.g. Monte Carlo sampling) to insert a distribution of defects and impurities). In other cases we can use a force field with molecular dynamics to in a process of heating and cooling to randomize and then annual the system. These techniques can be used to generate an ensemble of structures that can then be computed using QM and MD to determine the significant ones for subsequent analysis.

Fundamental rate parameter data, obtained from QM calculations or from MD calculations or elsewhere in step 220, are used to model the characteristics of collective systems incorporating distributions of several or many kinds of defects and impurities using molecular dynamics (step 230). In this step, many systems incorporating defects and impurities distributed spatially in appropriate ways (e.g., to mimic conditions that could in principle be prepared experimentally) can be considered in order to construct an ensemble of systems to mimic practical or experimentally interesting systems. These systems can be constructed as described above. These calculations then use the fundamental rate parameter data from QM and elsewhere to estimate the rates for microscopic, mesoscale, and macroscopic systems containing distributions of such defects and impurities to determine defect-dopant dynamics.

In one implementation, these calculations are performed using kinetic Monte Carlo (kMC) dynamics in which the various independent rates are used to evolve the system while allowing multiple time scales to provide a practical means for describing a variety of processing conditions. The multiscale kMC simulation provides information about the long-term consequences of defect/dopant reactions, indicating which clusters constitute major components and identifying the important reaction pathways.

The fundamental data (e.g. from the QM calculations in step 220) and reaction information (e.g. from the kMC dynamics calculations in step 230) are used to predict the distribution of dopant and defect components and clusters (step 240). Equilibrium and nonequilibrium distributions of these components are predicted as a function of initial concentrations, temperature, and other external conditions (e.g. stress, voltage, magnetic fields, electromagnetic fields, temperature profiles, external radiation). The predicted distributions are solved as a function of time and processing conditions with a hierarchy of methods that in addition to the atomistic approaches (QM, MD) mentioned above may involve partial differential equations using finite elements and continuum approaches along with atomistic conditions.

Processing operations can involve many components, including dopants, defects and clusters or complexes as discussed above, the concentrations of which at a given time can be interdependent. Thus, for example, ion implantation of boron in a silicon lattice creates many species, including substitutional and interstitial boron atoms, interstitial silicon atoms, vacancies, and clusters of various numbers of boron and silicon atoms. Some of these species, referred to here as "fast" or "ultrafast" species or components, can have very high diffusivity or dissociation rates (which can be estimated according to the diffusion energy barrier and binding energy, respectively), such that the local concentration of these species will vary significantly with time as they either diffuse away or dissociate into other components.

As the system evolves in time, some fast processes may achieve a steady state in which the relative concentrations are nearly constant with only the overall population changing slowly with time. In such circumstances the atomistic dynamics may be replaced with a constitutive equation whose parameters are determined from the atomistic equations. This can allow the longer time phenomena to be described in terms of a mesoscale or continuum equation, greatly extending the time and length scales that are practical.

Thus, the concentration of fast species can be described as follows:

$$\frac{\partial C_k}{\partial t} = \nabla(D_k \nabla C_k) + K_{R,ij} C_i C_j + K_{D,m} C_m - K_{R,kl} C_k C_l - K_{D,k} C_k$$

where $D_k$ and $C_k$ are the diffusivity and the concentration of the component k, respectively, and the reaction and dissolution coefficients are given by $$K_{R,ij} = 4\pi R_p(D_i + D_j)$$

$$K_{D,k} = \frac{n_H}{4} K_{R,ij} \exp\left(-\frac{E_{b,k}}{k_B T}\right)$$

where, $R_p$ is the capture radius, $n_H$ is the concentration of lattice sites, and $E_b$ is the dissociation energy of k into i and j. In the above equation, the first term on the right-hand side represents diffusion; the second and third terms are generation by i+j clustering (i+j→k) and m dissolution (m→k+l), respectively. The k component can be removed from the process according to the reverse processes, as described by the fourth (k→i+j) and the fifth (k+l→m) terms.

At the onset of a process such as annealing the fast components are far from thermal equilibrium with other slowly varying species (i.e., so-called "slow" components, or species that have a large binding energy or low diffusivity). To describe the dynamics of these fast components, the partial differential equation set out above must be solved using a very small time step (which can be estimated as at least an order of magnitude or more smaller than the lowest simulation time scale, which, in turn, can be approximated by $\Delta x^2/D$ or $1/kd$, where $\Delta x$ represents the mesh size of the simulation). Thus, for example, at 1000° C., a time step of on the order of $10^{-12}$ sec may be required for describing the dynamics of single Si interstitials, $B_s$—$Si_i$ pairs or vacancies in the silicon lattice. To describe the concentration decay of such components using such small time steps can be computationally intensive for typical simulation time scales of larger than 1 sec., such that a typical simulation involving a significant number of fast components can take hours or more of computation time.

Computation times can be significantly reduced, however, by recognizing that the fast components typically reach thermal equilibrium with slow components, a so-called pseudo steady state in which their concentrations are essentially determined by those of the slow components. At this stage, the concentration of the fast components thus can be determined by solving an ordinary differential equation:

$$\nabla(D_k\nabla C_k)+K_{R,ij}C_iC_j+K_{D,m}C_m-K_{R,kl}C_kC_l-K_{D,k}C_k=0$$

That is, at times before the pseudo steady state is reached for a given fast component, the concentration variation of that fast component is described by solving a partial differential equation with a small time step as described above, whereas once the fast component arrives at the pseudo steady state its concentration can be determined by solving an ordinary differential equation that involves slowly varying components.

At this stage the time step can be adjusted to fit the next fastest component (e.g., according to the diffusivities and the dissociation rates of next fastest components). By decoupling the fast components reaching a pseudo steady state, the time step can be continuously increased. By contrast, the concentrations of slow components are determined simply by solving the relevant partial differential equation with an appropriate time step, which should be significantly larger due to the larger binding energies and lower diffusivities of these species and therefore not as computationally intensive as for the fast components.

In this way, the computational time can be substantially reduced, which in turn allows an computationally efficient (cost-effective) determination and prediction of non-equilibrium processes that may involve time scales ranging from picoseconds to minutes. Furthermore such computational efficiency opens the door to large-scale two- and three-dimensional simulations indispensable for optimizing processing conditions of actual devices.

EXAMPLE

Modelling Ultrashallow Junction Processing

The application of a multiscale simulation method such as that described above to ultrashallow junction processing—and in particular the ultrashallow deposition of boron in silicon—will now be described with reference to FIGS. 3–9. This example considers the possible distributions of boron, silicon, and vacancies at various substitutional and interstitial sites, including clusters of several atoms and/or defects at any one site. The application of multiscale modeling for ultrashallow junction processing is summarized in FIG. 3.

1. Microscopic Processes: Quantum Mechanics

We first used quantum mechanics calculations 310 to model the relevant microscopic processes. All atomic structures were optimized using the local density approximation (LDA) (D. M. Ceperley and B. J. Alder, *Phys. Rev. Lett.* 45, 566 (1980); J. Perdew and A. Zunger, *Phys. Rev. B* 23, 5048 (1981)) to density functional theory (DFT), as implemented in the CPMD V3.3 package. Calculation of the energetics of the LDA structures using the generalized gradient approximation (GGA) (J. P. Perdew et al., Phys. Rev. Lett. 77, 3865 (1996)) gave similar results. We used a non-local, norm-conserving pseudopotential (S. Goedecker et al., *Phys. Rev. B* 54, 1703 (1996)) and a plane-wave cutoff energy of 20 Ry. The defect systems considered were modeled using a 192-atom supercell with a fixed volume that yields a Si—Si bond distance of 2.35 Å in pure silicon. All atomic positions were allowed to relax fully until all residual forces were smaller than $5\times10^{-4}$ Hartree/Bohr. Because of the large supercell, we use just one k-point at Γ for the Brillouin-zone (BZ) integrations. Of course the details (eg number of k points) may be different for other systems. Generally one considers a range of such parameters for prototype systems to choose the parameters providing acceptable accuracy at acceptable costs. As described above many computational programs are available for such detailed QM calculations.

Figure 4:
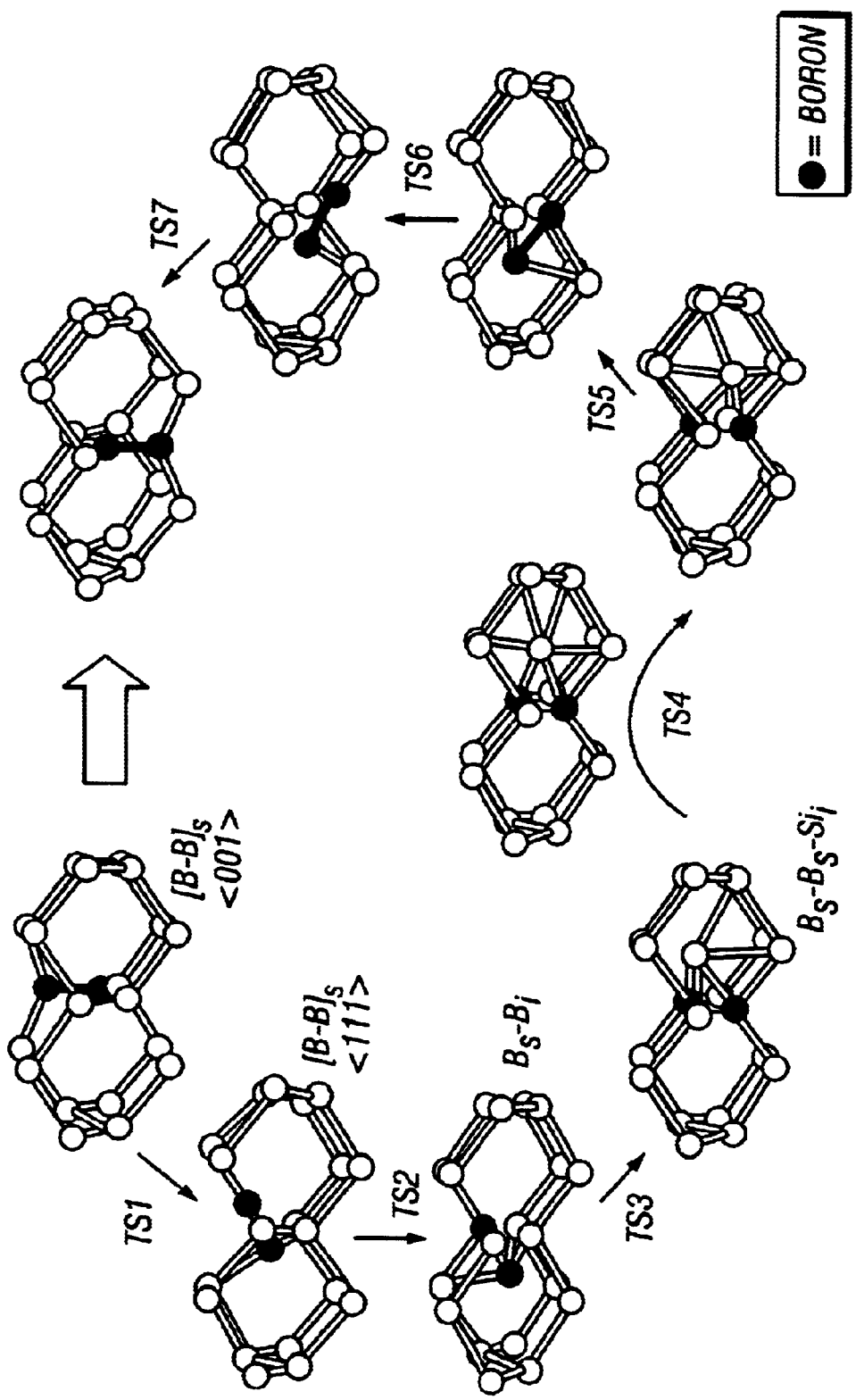
FIG. 4 illustrates structures along a predicted reaction pathway for diffusion of a boron—boron pair in silicon.

Such methods (QM, MD, etc.) are used first to elicit an improved understanding of defect—defect and defect-dopant interactions, which is essential for developing a comprehensive model of junction processing. In particular, for the example under consideration here we needed to understand how boron doping for ultrashallow p-type junctions in silicon brings about many complex diffusion phenomena associated with boron—boron and boron-silicon interstitial clustering. Since ultrashallow junction fabrication requires a very high doping level (e.g. $>10^{20}$ cm$^{-3}$) such clustering may be unavoidable. Since silicon clusters are known to be a main source for single silicon interstitials that are primarily responsible for the transient enhanced diffusion (TED) of boron, it is essential to develop a concrete model for the formation of silicon interstitial clusters during implantation and at the onset of annealing. We have shown that Quantum mechanics calculations (implementing density functional theory) are able to identify the key fundamental processes. Such studies are an essential part of our method. In particular, for our example system we determined the following fundamental processes:

Diffusion of a boron—boron pair (substitutional-interstitial, $B_s$—$B_i$)
  Dissolution of the $B_s$—$B_s$—$B_i$ complex
  Catalytic role of boron in silicon self interstitial clustering $B_s$—$B_i$ diffusion—Using QM we found that di-boron diffusion plays an important role in determining diffusion profiles during ultrashallow junction processing (which requires high boron-dopant concentration as well as high annealing temperature). FIG. 4 illustrates a reaction pathway along which a di-boron pair diffuses from one lowest energy configuration of [B—B]$_s$-<001>to an equivalent structure at an adjacent equivalent site through three local minimum states denoted as: [B—B]$_s$-<111>, $B_s$—$B_i$, and $B_s$—$B_s$—$Si_i$. In this way the number of broken bonds and distortions can be kept at a minimal during the course of the B—B diffusion. The activation energy for the diffusion is estimated to be 1.87 eV in the local density approximation (1.81 eV in the generalized gradient approximation).

Figure 5:
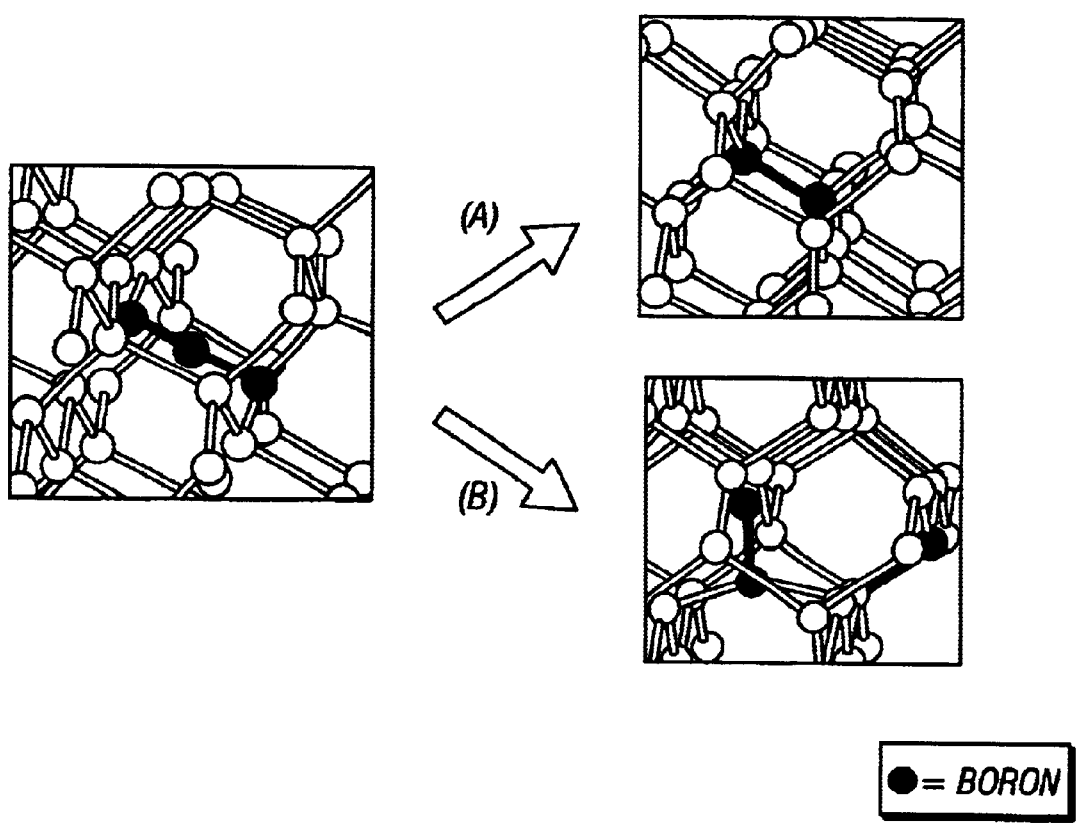
FIG. 5 illustrates predicted mechanisms for the most stable boron cluster, $B_s$—$B_s$—$B_i$ (a) by $B_i$ diffusion; (b) by $B_s$ diffusion.

$B_s$—$B_s$—$B_i$ dissolution—The $B_s$—$B_s$—$B_i$ complex has been known to be the most stable among boron containing clusters in silicon. The $B_s$—$B_s$—$B_i$ complex could dissolve into $B_s$—$B_s$ and $B_i$, i.e., a mobile boron atom escapes while leaving the $B_{s-Bs}$ complex behind; the $B_i$ binding energy is approximated to be 4.0 eV. We have also found that the $B_s$—$B_s$—$B_i$ can be dissociated into $B_s$—$B_i$ and $B_s$ as a result of the diffusion of $B_s$ to the nearest neighbor sites. FIG. 5 illustrates possible mechanisms of $B_s$—$B_s$—$B_i$ dissolution (by $B_i$ diffusion, path (a), or $B_s$ diffusion, path (b)). In addition, our calculations suggest that the conversion of $B_s$—$B_s$—$B_i$ into $B_s$—$B_i$—$B_i$ by capturing a Si interstitial would substantially lower thermal budget for the dissolution of the three-boron cluster; the $B_i$ binding energy of 1.0 eV for $B_s$—$B_i$—$B_i$ is far smaller than that of 4.0 eV for $B_s$—$B_s$—$B_i$. This is consistent with experiments that show facilitation in boron cluster dissolution with increasing the number of Si interstitials.

Figure 6:
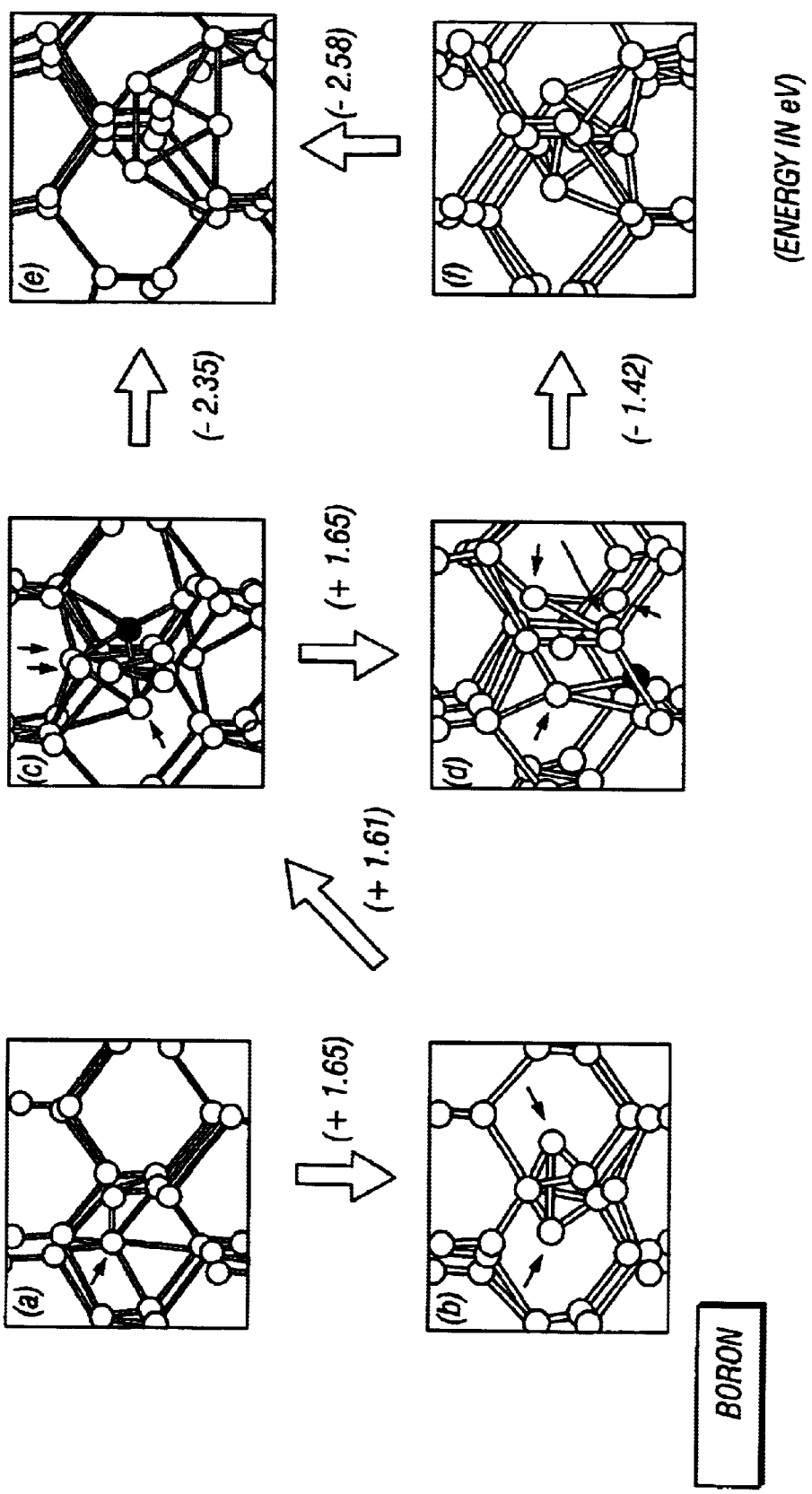
FIG. 6 illustrates predicted clustering and dissolution of B—$Si_i$ clusters (a) $B_s$—$Si_i$; (b) $B_s$—$Si_{i,2}$; (c) $B_s$—$Si_{i,3}$; (d) $B_s$—$Si_{i,4}$; (e) $Si_{i,2}$; (f) $Si_{i,3}$.

Catalytic role of boron in self-interstitial clustering—Single Si interstitials can be captured by a boron substitutional to form a $B_s$—$Si_i$ pair; we calculate that the binding energy of $B_s$—$Si_i$ is about 1.0 eV. The $B_s$—$Si_i$ pair can be further stabilized by capturing another single Si interstitials; we calculate that the binding energy of $Si_i$ with $B_s$—$Si_i$ is about 1.6 eV. Such B—$Si_{i,x}$ complexes capture and stabilize mobile Si interstitials. On the other hand the binding energy of B becomes weaker with the number of Si interstitials incorporated. This implies that the boron atom can eventually escape at the expense of low energy barrier. As a whole, boron atoms may play a role as a catalyst for Si interstitial clustering. FIG. 6 illustrates neutral state B—$Si_{i,x}$ complexes (x=1–4; (a) $B_s$—$Si_i$; (b) $B_s$—$Si_{i,2}$; (c) $B_s$—$Si_{i,3}$; (d) $B_s$—$Si_{i,4}$; (e) $Si_{i,2}$; (f) $Si_{i,3}$), together with the binding energy of single Si interstitial and boron. This finding provides insight into how small silicon clusters can be produced at the early stage of annealing.

2. Defect-Dopant Dynamics: Kinetic Monte Carlo

Referring again to FIG. 3, kinetic Monte Carlo molecular dynamics simulations 320 were used to describe dopant diffusion and defect-dopant interactions. In these calculations, the locations of defect, dopant, and clusters can be traced as a function of time for time scales of multiscale simulations ranging from $10^{-12}$ sec to $10^2$ sec, all in one simulation on one processor in a few minutes. All entities are treated as point-like particles with basic attributes of diffusivity and dissociation rate. We based the data for these kMC simulations (e.g. the temperature-dependent diffusivities of mobile species and the binding energies of clusters) mainly on ab initio QM calculations. The temperature dependence of the diffusivity can be written as $$D_{diss} = D_o \exp(-E_m/k_B T)$$

Here $D_{diff}$ is the diffusivity, $D_o$ is the prefactor, $E_m$ is the diffusion energy barrier, $k_B$ is the Boltzmann constant, and T is the substrate temperature. In a similar way a dissociation rate can be represented by $$D_{diss} = D_o \exp(-(E_m + E_b)/k_B T)$$

where $E_b$ is the binding energy of a leaving mobile species with a remaining entity.

Figure 7:
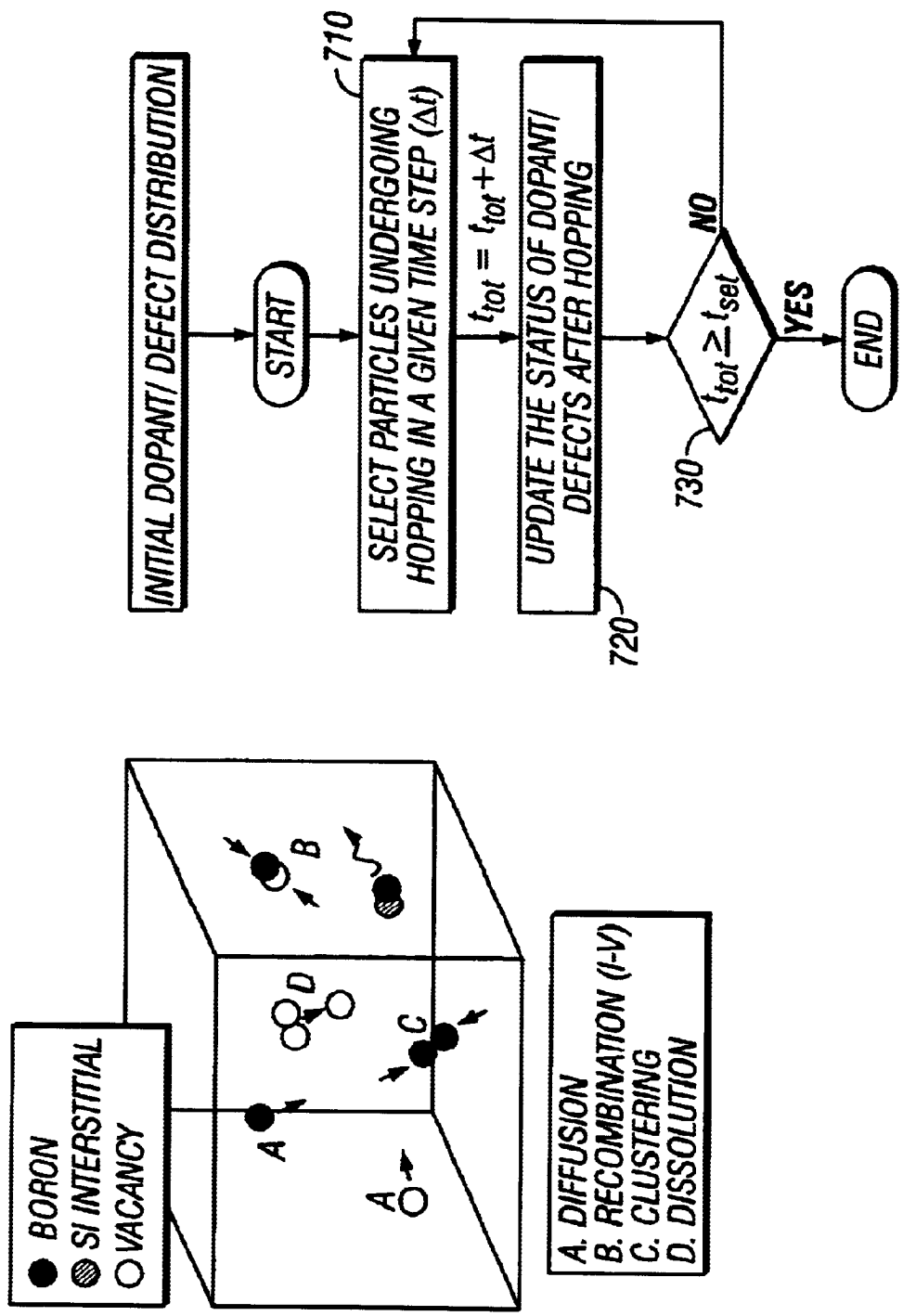
FIG. 7 illustrates a schematic diagram of a kinetic Monte Carlo simulation according to the present invention.

FIG. 7 illustrates a schematic diagram of the kMC simulation. During this simulation various defect-dopant dynamics including clustering and dissociation are all allowed to occur. At each time step, we first choose all possible events taking place in the simulation box (step 710). Then we update the status of each particle (step 720). These steps are repeated (the NO branch of step 730) until the total simulation time reaches a specified amount (the YES branch of step 730).

Figure 8:
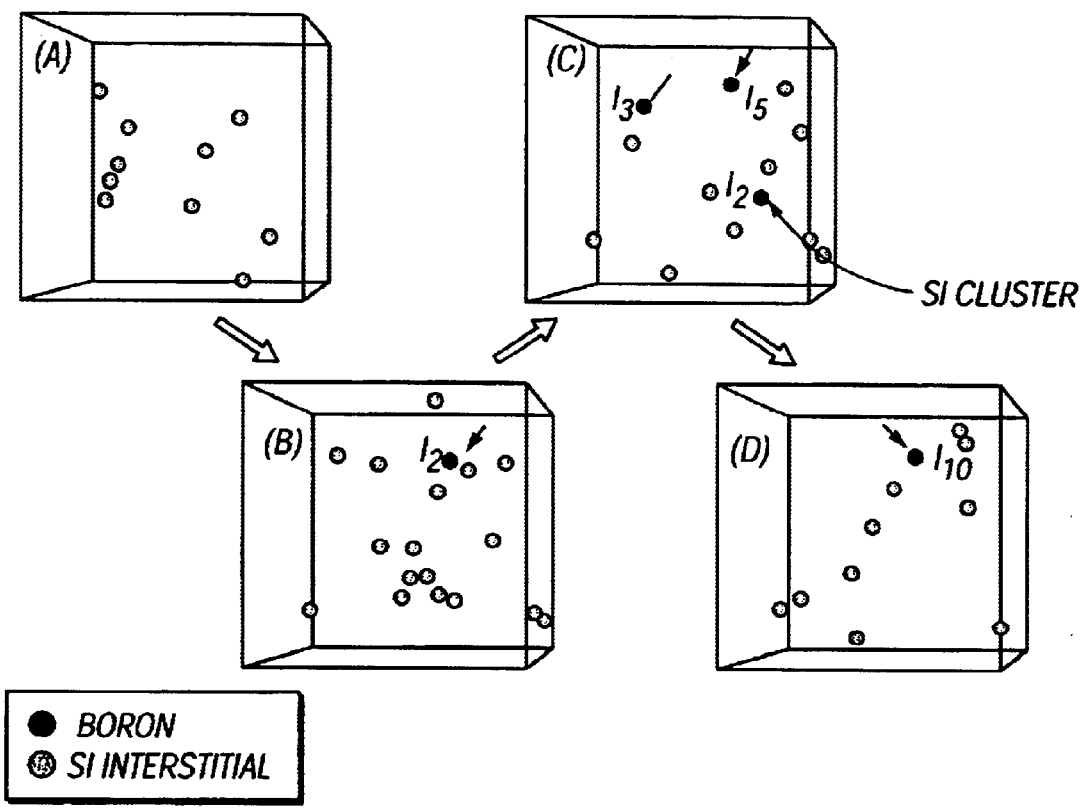
FIG. 8 illustrates the results of a kinetic Monte Carlo simulation for $C_B = C_{sii} = 10^{19}$ cm$^{-3}$, T=900 K (a) t=0 sec; (b) t=$10^{-6}$ sec; (c) t=$10^{-3}$ sec; (d) t=$10^0$ sec.

FIG. 8 illustrates the result of a kMC simulation. Starting with $B_s$—$Si_i$ pairs at a of concentration $10^{19}$ cm$^{-3}$, we performed the kMC simulation at 900 K. After 1 μsec, most of the $B_s$—$Si_i$ pairs are dissociated and Si interstitials begin to form clusters. The silicon clusters get bigger to become more stable with annealing time. Finally all small clusters disappear and form a bigger one, demonstrating Ostwald ripening. This kMC simulation illustrates how defects and dopants behave during high-temperature thermal treatment. Such visualization of atomic scale processes help one to understand defect-dopant dynamics. However, such kMC approaches can be limited in describing accurately the doping profile evolution while taking into account a significant variation in the concentration of species ranging from $10^0$ to $10^{21}$ cm$^3$. To address this problem in multiscale simulations, we also developed the continuum-based model, addressed next.

3. Doping Profile Evolution: Continuum Mechanics

Returning to FIG. 3, we modeled the evolution of the macroscopic doping profile using continuum mechanics 330. As discussed above, the set of nonequilibrium reactions is described as follows $$\frac{\partial C_k}{\partial t} = \nabla(D_k \nabla C_k) + K_{R,ij} C_i C_j + K_{D,m} C_m - K_{R,kl} C_k C_l - K_{D,k} C_k$$

where $D_k$ and $C_k$ are the diffusivity and the concentration of the component k, respectively, and the reaction and dissolution coefficients are given by $$K_{R,ij} = 4\pi R_p (D_i + D_j)$$

$$K_{D,k} = \frac{n_H}{4} K_{R,ij} \exp\left(-\frac{E_{b,k}}{k_B T}\right)$$

where, $R_p$ is the capture radius, $n_H$ is the concentration of Si lattice sites (~$5 \times 10^{22}$ cm$^{-3}$), and $E_b$ is the dissociation energy of k into i and j.

In these simulations, it is assumed that boron exists in the form of either $B_s$—Si or $B_s$—$Si_2$ at the onset of annealing. The capture radius ($R_p$) is set to be $2.5 \times 10^{-8}$ cm. Self interstitials, B—$Si_i$ pairs, and Bs-Bi pairs are allowed to diffuse at a diffusion rate of $0.005 \times \exp(-0.4$ eV/$k_B T)$, $0.001 \times \exp(-0.68$ eV/$k_B T)$, $1.5 \times \exp(-2.45$ eV/$k_B T)$ cm$^2$/sec, respectively. The dissociation rates of key defect-dopant complexes, $B_s$—$Si_i$, $B_s$—$B_i$, $B_s$—$B_s$—$B_i$, are estimated to be $10^{13} \exp(-1.15$ eV/$k_B T)$, $3 \times 10^{13} \exp(-2.18$ eV/$k_B T)$, $10^{17} \exp(-4.46$ eV/$k_B T)$ sec$^{-1}$, respectively. Other boron-interstitial complexes (considered in the simulations) include $B_s$—$Si_{i,2}$, $B_s$—$Si_{i,3}$, Bs$_s$—$B_{i,2}$, $B_s$—$B_{i,3}$, $B_s$—$B_i$—$Si_i$, $B_s$—$B_i$—$Si_{i,2}$, $B_{s,2}$—$B_i$, and $B_{s,2}$—$B_{i,2}$.

As discussed above, the algorithm used to describe macroscopic doping profile evolution while taking into account ultrafast microscopic processes (diffusion, clustering, dissolution) incorporates the concept of a pseudo steady state for defect and dopant components whose concentration varies very rapidly with time. At the onset of high-temperature annealing there may be a large number (far beyond equilibrium) of ultrafast components such as Si self-interstitials, vacancies, and $B_s$—$Si_i$ pairs that have either high diffusivity or high dissociation rate. To describe the concentration decay of such components requires a very small time step. For example, at 1000° C., typically a time step of $10^{-12}$ sec is required for describing the dynamics of single Si interstitials and vacancies. Also the high dissociation rate of $B_s$—$Si_i$ pairs ($\approx 10^9$ sec$^{-1}$) requires a small time step (of far less than $10^{-9}$ sec) to calculate the $B_s$—$Si_i$ concentration variation. The time step must be decreased further as the annealing temperature increases. Within $10^{-9}$ to (at most) $10^{-6}$ sec, however, the so called fast components reach a pseudo steady state in which their concentrations are determined by other slowly varying components. That is, before the pseudo steady state the concentration variation of such fast components is described by solving a partial differential equation with a small time step (preferably smaller than $\Delta x^2/D_i$ and $1/k_{d,i}$, where $\Delta x$ is a mesh size, $D_i$ and $k_{d,i}$ are the diffusivity and the dissociation rate of the fast components); e.g., for $B_s$—Si:

$$\frac{dC_{B_s-Si}}{dt} = -D_{B_s-Si}\frac{d^2 C_{B_s-Si}}{dx} + g_{B_s-Si} - l_{B_s-Si}$$

where $$g_{B_s-Si}=D_{Si}R_pC_{Si}C_{B_s}+k_{d,B_s-Si_2}C_{B_s-Si_2}+k_{d,B_s-B_2}C_{B_s-B_i}+k_{d,B_s,2-B_2,2}C_{B_s,2-B_i,2}$$

$$l_{B_s-Si}=D_{Si}R_pC_{Si}C_{B_s-Si}+D_{B_s-Si}R_pC_{B_s-Si}(C_{B_s}+C_{B_s-B_i}+C_{B_s-B_{2i}}+C_{B_s-Si_2}+C_{B_s,2-B_s}+\ldots) +k_{d,B_s-Si}C_{B_s-Si}$$

here $C_i$, $D_i$, and $k_{d,i}$ are the concentration, the diffusivity, and the dissociation rate of species i. However, once the fast components arrive at the pseudo steady state their concentrations are determined by solving an ordinary differential equation that involves slowly varying components; e.g., for $B_s$—Si, $$0 = -D_{B_s-Si}\frac{d^2 C_{B_s-Si}}{dx} + g_{B_s-Si} - l_{B_s-Si}$$

At this stage the time step can be adjusted to fit the next fastest component (e.g., according to the diffusivities and the dissociation rates of next fastest components). By decoupling the fast components reaching a pseudo steady state, the time step can be continuously increased.

Figure 9:
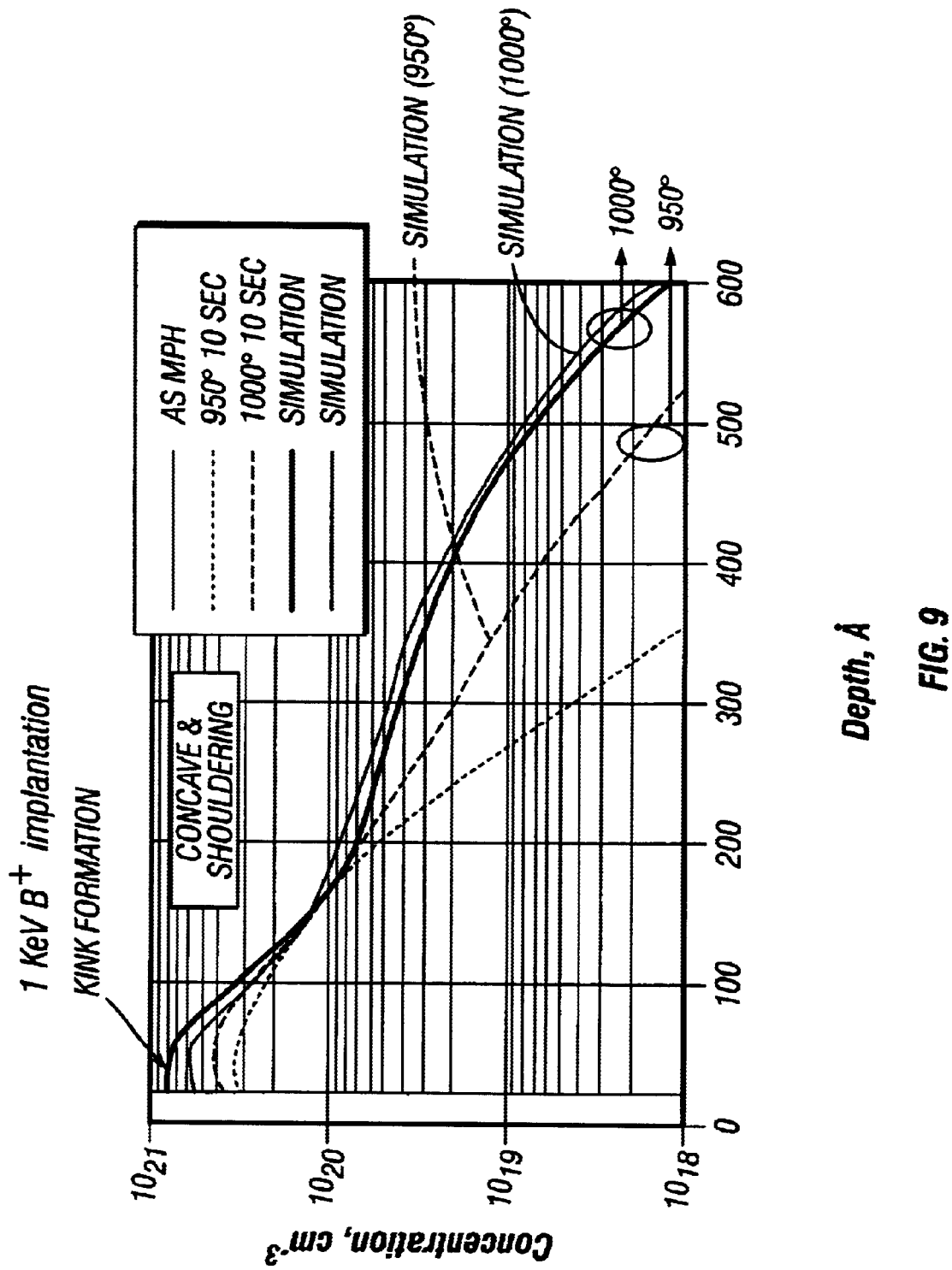
FIG. 9 illustrates a comparison of simulations and experiments for two different annealing temperatures, 950° C. and 1000° C.

A comparison of simulations with experiments for two different annealing temperatures, 950° C. and 1000° C., is illustrated in FIG. 9. Boron atoms are injected by 1 keV B$^+$implantation. Simulation results are in good agreement with experiments; theses simulations successfully capture key features of diffusion profiles including 'kink' and concave-shouldering.

Kink formation—We have found that the kink at the near surface is mainly due to the diffusion of $B_s$—$Si_i$ pairs towards the surface followed by precipitation at the early stage of annealing. After implantation (i.e., before high temperature thermal annealing) most of boron atoms remain in the form of $B_s$—$Si_i$. At the onset of annealing $B_s$—$Si_i$ pairs begin to form boron clusters in the high concentration region. However a large fraction of $B_s$—$Si_i$ pairs at near surface can escape to the surface and then undergo precipitation in the surface region.

Concave-shouldering behavior—The intriguing feature is attributed to slow dissolution of boron clusters and fast diffusion of mobile boron complexes. Our simulations demonstrate that $B_s$—$B_s$—$B_i$ and $B_s$—$B_i$ are mainly responsible for the slow dissolution and the fast diffusion, respectively.

These calculations demonstrate multiscale simulations ranging from $10^{12}$ sec to $10^2$ sec, all in one simulation on one processor in a few minutes. This makes it practical to consider on currently available computer systems large-scale two- and three-dimensional simulations on realistic models of devices the geometries and processing conditions that would be useful for optimizing processing conditions of actual devices. For example, numerous DeN-PEM calculations can be carried out considering a variety of possible processing conditions (e.g. different exposures to dopants, temperature, times, fields) to determine the conditions leading to optimum characteristics and properties. After testing this design experimentally, predicted characteristics can be monitored in situ in the manufacturing process to control operating conditions at the optimum values and to check the products for optimum manufacture without the necessity of complex measurements or device fabrication.

The invention can be implemented in digital electronic circuitry, or in computer hardware, firmware, software, or in combinations of them. Apparatus of the invention may be implemented in a computer program product tangibly embodied in a machine-readable storage device for execution by a programmable processor. Method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing may be supplemented by, or incorporated in specially-designed ASICs (application-specific integrated circuits).

A number of embodiments of the invention have been described. Nevertheless, it will be understood that various modifications may be made without departing from the spirit and scope of the invention. Accordingly, other embodiments are within the scope of the following claims.

What is claimed is:

1. A computer implemented method for predicting the behavior of dopant and defect components in a substrate lattice formed from a substrate material, the method comprising:

obtaining fundamental data for a set of microscopic processes that can occur during one or more material processing operations, the fundamental data including data representing the kinetics of processes in the set of microscopic processes and the energetics and structure of possible states in the material processing operations; and predicting a distribution of dopant and defect components in the substrate lattice based on the fundamental data and a set of external conditions, the distribution of one or more first components being predicted by calculating for each first component the concentration of the first component for a time period before the first component reaches a pseudo steady state by solving a first relationship and calculating the concentration of the first component for a time period after the first component reaches the pseudo steady state by solving a second relationship based on one or more second components, the pseudo steady state being a state in which the concentration of the fast component is determined by concentrations of the one or more second components.

2. The method of claim 1, wherein:
the one or more first components include fast components having a high diffusivity or a high dissociation rate and the one or more second components include slow components having a low diffusivity or a low dissociation rate.

3. The method of claim 2, wherein:
for each of the first components, the first relationship is solved with a time step determined based on the diffusivity and the dissociation rate of the corresponding first component.

4. The method of claim 3, wherein:
the first relationship is an equation:

$$\frac{\partial C_k}{\partial t} = \nabla(D_k \nabla C_k) + K_{R,ij} C_i C_j + K_{D,m} C_m - K_{R,kl} C_k C_l - K_{D,k} C_k$$

where $D_k$ and $C_k$ are the mobility and the concentration of a component k, respectively; the first term in the right-hand side represents diffusion of the component k; the second and third terms represents generation of the component k by i+j clustering (i+j→k) and m dissolution (m→k+l) respectively; and the fourth and fifth terms represent destruction of the component k by (k+l→m) and (k→i+j), respectively; and the clustering and dissolution coefficients are given by $$K_{R,ij} = 4\pi R_p (D_i + D_j)$$

$$K_{D,k} = \left(\frac{n_H}{4}\right) K_{R,ij} \exp\left(-\frac{E_{b,k}}{k_B T}\right)$$

where $R_p$ is the capture radius, $n_H$ is the concentration of lattice sites in the substrate lattice, $E_b$ is the dissociation energy of k into i and j, $k_B$ is the Boltzmann constant, and T is the substrate temperature of the substrate lattice.

5. The method of claim 4, wherein:
the second relationship is an equation:

$$\nabla(D_k \nabla C_k) + K_{R,ij} C_i C_j + K_{D,m} C_m - K_{R,kl} C_k C_l - K_{D,k} C f_k = 0.$$

6. The method of claim 5, further comprising:
calculating, based on the fundamental data, reaction information identifying one or more major components and reactions from a set of possible components and one or more major reaction pathways for the processes of the set of microscopic processes;
wherein the distribution of dopant and defect components in the substrate lattice is predicted based on the fundamental data, the external conditions and the reaction information.

7. The method of claim 5, wherein:
the microscopic processes include diffusion, clustering and dissociation of dopant and/or defect components in the substrate lattice.

8. The method of claim 5, wherein:
the fundamental data includes data representing the dissolution rate of defect components, the mobility of mobile species and the binding energy of clusters.

9. The method of claim 5, wherein:
the set of external conditions includes initial concentrations for each dopant and defect component, and an initial temperature.

10. The method of claim 5, wherein:
the material processing operations include one or more of heat treatments, oxidation, exposure to impurities, or changes in pressure, stress, voltage, magnetic fields, electromagnetic radiation or ultrasonic radiation.

11. The method of claim 5, wherein:
the fundamental data is calculated in a quantum mechanics calculation.

12. The method of claim 6, wherein:
the reaction information is calculated in a kinetic Monte Carlo simulation.

13. The method of claim 5, wherein:
predicting the distribution of dopant and defect components in the substrate lattice includes predicting a plurality of distributions of dopant and defect components in the substrate lattice for each of a plurality of different sets of external conditions.

14. The method of claim 13, further comprising:
selecting a desired distribution from the plurality of predicted distributions; and
controlling a manufacturing process based on the set of external conditions corresponding to the selected distribution.

15. The method of claim 5, wherein:
the one or more material processing operations define a procedure for boron doping of silicon substrates; and
the set of microscopic processes include the formation, diffusion and dissolution of substitutional boron-interstitial boron pairs in a silicon substrate lattice.

16. A computer program product, tangibly stored on a computer-readable medium, for predicting the behavior of dopant and defect components in a substrate lattice formed from a substrate material, comprising instructions operable to cause a programmable processor to:

obtain fundamental data for a set of microscopic processes that can occur during one or more material processing operations, the fundamental data including data representing the kinetics of processes in the set of microscopic processes and the energetics and structure of possible states in the material processing operations; and predict a distribution of dopant and defect components in the substrate lattice based on the fundamental data and a set of external conditions, the distribution of one or more first components being predicted by calculating for each first component the concentration of the first component for a time period before the first component reaches a pseudo steady state by solving a first relationship and calculating the concentration of the first component for a time period after the first component reaches the pseudo steady state by solving a second relationship based on one or more second components, the pseudo steady state being a state in which the concentration of the fast component is determined by concentrations of the one or more second components.

17. The computer program product of claim 16, wherein:
the one or more first components include fast components having a high diffusivity or a high dissociation rate and the one or more second components include slow components having a low diffusivity or a low dissociation rate.

18. The computer program product of claim 17, wherein:
for each of the first components, the first relationship is solved with a time step determined based on the diffusivity and the dissociation rate of the corresponding first component.

19. The computer program product of claim 18, wherein:
the first relationship is an equation:

$$\frac{\partial C_k}{\partial t} = \nabla(D_k \nabla C_k) + K_{R,ij}C_iC_j + K_{D,m}C_m - K_{R,kl}C_kC_l - K_{D,k}C_k$$

where $D_k$ and $C_k$ are the mobility and the concentration of a component k, respectively; the first term in the right-hand side represents diffusion of the component k; the second and third terms represents generation of the component k by i+j clustering (i+j→k) and m dissolution (m→k+l), respectively; and the fourth and fifth terms represent destruction of the component k by (k+l→m) and (k→i+j) respectively; and the clustering and dissolution coefficients are given by $$K_{R,ij} = 4\pi R_p(D_i + D_j)$$

$$K_{D,k} = \left(\frac{n_H}{4}\right)K_{R,ij}\exp\left(-\frac{E_{b,k}}{k_B T}\right)$$

where $R_p$ is the capture radius, $n_H$ is the concentration of lattice sites in the substrate lattice, $E_b$ is the dissociation energy of k into i and j, $k_B$ is the Boltzmann constant, and T is the substrate temperature of the substrate lattice.

20. The computer program product of claim 19, wherein:
the second relationship is an equation:

$$\nabla(D_k\nabla C_k)+K_{R,ij}C_iC_j+K_{D,m}C_m-K_{R,kl}C_kC_l-K_{D,k}C_k=0.$$

21. The computer program product of claim 20, further comprising instructions operable to cause a programmable processor to:
calculate, based on the fundamental data, reaction information identifying one or more major components and reactions from a set of possible components and one or more major reaction pathways for the processes of the set of microscopic processes;
wherein the distribution of dopant and defect components in the substrate lattice is predicted based on the fundamental data, the external conditions and the reaction information.

22. The computer program product of claim 20, wherein:
the microscopic processes include diffusion, clustering and dissociation of dopant and/or defect components in the substrate lattice.

23. The computer program product of claim 20, wherein:
the fundamental data includes data representing the dissolution rate of defect components, the mobility of mobile species and the binding energy of clusters.

24. The computer program product of claim 20, wherein:
the set of external conditions includes initial concentrations for each dopant and defect component, and an initial temperature.

25. The computer program product of claim 20, wherein:
the material processing operations include one or more of heat treatments, oxidation, exposure to impurities, or changes in pressure, stress, voltage, magnetic fields, electromagnetic radiation or ultrasonic radiation.

26. The computer program product of claim 20, wherein:
the fundamental data is calculated in a quantum mechanics calculation.

27. The computer program product of claim 21, wherein:
the reaction information is calculated in a kinetic Monte Carlo simulation.

28. The computer program product of claim 20, wherein:
the instructions operable to cause a programmable processor to predict the distribution of dopant and defect components in the substrate lattice include instructions operable to cause a programmable processor to predict a plurality of distributions of dopant and defect components in the substrate lattice for each of a plurality of different sets of external conditions.

29. The computer program product of claim 28, further comprising instructions operable to cause a programmable processor to:
select a desired distribution from the plurality of predicted distributions; and control a manufacturing process based on the set of external conditions corresponding to the selected distribution.

30. The computer program product of claim 20, wherein:
the one or more material processing operations define a procedure for boron doping of silicon substrates; and
the set of microscopic processes include the formation, diffusion and dissolution of substitutional boron-interstitial boron pairs in a silicon substrate lattice.

* * * * *